United States Patent [19]

Sternby

[11] Patent Number: 5,788,846
[45] Date of Patent: Aug. 4, 1998

[54] METHOD OF MEASURING THE EFFECT OF A DIALYSIS TREATMENT

[75] Inventor: Jan Sternby, Lund, Sweden

[73] Assignee: Gambro AB, Sweden

[21] Appl. No.: 593,536

[22] Filed: Jan. 29, 1996

Related U.S. Application Data

[63] Continuation of Ser. No. 206,548, Mar. 4, 1994, abandoned.

[30] Foreign Application Priority Data

Mar. 5, 1993 [SE] Sweden .................... 9300728

[51] Int. Cl.$^6$ .................... B01D 61/32; B01D 61/34; A61M 1/14
[52] U.S. Cl. .................... 210/647; 210/321.65; 210/645; 210/646; 210/929
[58] Field of Search .................... 210/645, 646, 210/647, 746, 321.65, 929; 604/4, 5, 6; 73/861.07, 863, 863.01, 863.02, 863.03

[56] References Cited

U.S. PATENT DOCUMENTS

| | | | |
|---|---|---|---|
| 4,231,366 | 11/1980 | Schael | 128/DIG. 13 |
| 4,897,184 | 1/1990 | Shouldice et al. | 210/87 |
| 5,024,756 | 6/1991 | Sternby | 210/647 |
| 5,100,554 | 3/1992 | Polaschegg | 210/647 |
| 5,110,477 | 5/1992 | Howard et al. | 210/647 |
| 5,230,702 | 7/1993 | Lindsay et al. | 604/4 |
| 5,308,315 | 5/1994 | Khuri et al. | 604/4 |
| 5,404,761 | 4/1995 | Fellay et al. | 73/863.23 |
| 5,405,315 | 4/1995 | Khuri et al. | 210/646 |
| 5,507,723 | 4/1996 | Keshaviah | 604/5 |
| 5,518,623 | 5/1996 | Keshaviah et al. | 210/646 |

FOREIGN PATENT DOCUMENTS

| | | |
|---|---|---|
| 0495412 | 7/1992 | European Pat. Off. |
| 0504772 | 9/1992 | European Pat. Off. |
| 2457694 | 12/1980 | France |
| 2624384 | 12/1976 | Germany |
| 3436748 | 7/1985 | Germany |
| 3900119 | 8/1990 | Germany |

OTHER PUBLICATIONS

L.J. Garred, M. Rittau, W. McCready and B. Canaud, "Urea kinetic moldelling by partial dialysate collection," The Intern. Jour. of Artifical Organs, vol. 12, No. 2, 1986, pp. 96–102.

Primary Examiner—John Kim
Attorney, Agent, or Firm—Lerner, David, Littenberg, Krumholz & Mentlik

[57] ABSTRACT

Methods for measuring the effect of dialysis treatments are disclosed in which a fraction of the used dialysis fluid is extracted downstream of the dialyzer for analysis of at least one substance such as urea, and in which the fraction of dialysis fluid is extracted through a branch conduit containing a pump. In accordance with this method, the total amount of used dialysis fluid is measured and the concentration of that substance in the extracted fraction is measured, and the total amount of that substance removed from the patient can then be calculated from these values. This invention is preferably intended for use in connection with hemodialysis, hemofiltration and hemodiafiltration.

56 Claims, 1 Drawing Sheet

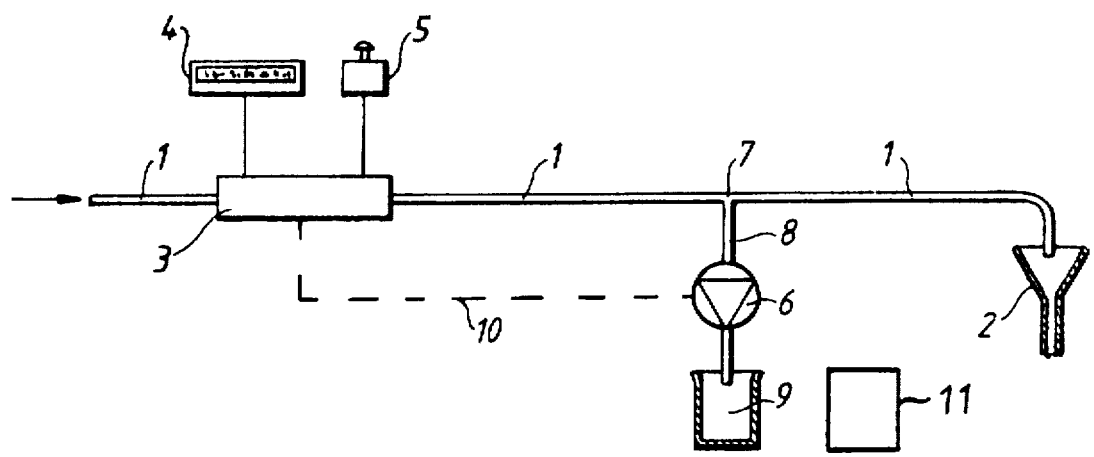

METHOD OF MEASURING THE EFFECT OF A DIALYSIS TREATMENT

This is a continuation of application Ser. No. 08/206,548 filed Mar. 4, 1994, abandoned.

FIELD OF THE INVENTION

The present invention relates to methods for measuring the effect of dialysis or similar treatments. More particularly, the present invention relates to methods of measuring such effects in which a fraction of the used dialysis fluid is extracted downstream of the dialyzer for analysis of at least one substance such as urea. More particularly, the present invention relates to such methods whereby the fraction of the dialysis fluid is extracted through a branch conduit containing a pump.

The present invention is primarily intended to be used in connection with hemodialysis, but can also be used in connection with systems such as hemofiltration and hemodiafiltration, which can be said to be somewhere between hemodialysis and hemofiltration, i.e., dialysis treatment utilizing a dialyzer having a permeability such that the patient needs to be supplied with a replacement fluid for the lost plasma water produced thereby.

BACKGROUND OF THE INVENTION

In the field of dialysis, it has become increasingly important, and consistently more common, to use some method to quantify the extent of dialysis which is administered to a patient. The most common such method is to utilize a method which has been referred to as "Urea Kinetic Modeling" (UKM). This method is based upon measurement of the level of urea in the blood, both before and after each treatment. These values are then employed in a theoretical model, which describes how the level of urea in the blood is changed during dialysis. In this model it is assumed that the degree of purification of the blood in the dialyzer is given by clearance K (including the remaining function of the kidneys), and that this leads to a similarly large concentration (c) of urea in the whole distribution volume (V) of same in the body. If one thus neglects the production of urea in the body, as well as the change in fluid volume during dialysis, one can then after a treatment time (T) arrive at a concentration of $$C_{after} = C_{before} * e^{-KT/V}$$

The coefficient KT/V is normally utilized as a measure of the administered dose of dialysis and can, in the above model, be calculated from the concentrations of urea both before and after the dialysis treatment has taken place. This model can be corrected for the production of urea by measuring the concentration at the start of the next dialysis, and can then also provide a measure of the urea production, which is an indirect measurement of the patient's protein intake.

The assumptions which underlie the above model do not, however, always correspond with what really occurs during dialysis, and the results of these calculations are therefore not particularly reliable. Particular uncertainty occurs with high efficiency treatments, i.e., when using highly permeable membranes. This has thus produced a great deal of controversy as to how one should conduct such measurements, and how one should calculate and utilize these results.

A better alternative method is to measure the amount of urea removed in the used dialysis fluid. This can be done by collecting the used dialysis fluid and measuring both the concentration of urea and the total amount of used dialysis fluid. In this way an exact value for the amount of removed urea can be obtained, and it can be done without the use of any theoretical model. The amount of urea removed in comparison to the weight of the body thus provides a correct value for the effect obtained through the dialysis. By periodic measurement of the urea in the blood, it can thus be ensured that the amount of urea in the body in the long run remains unchanged. In this manner the amount of urea which is removed also becomes a measure of the amount of urea produced, i.e., of the patient's protein intake.

To collect the entire amount of used dialysis fluid, however, is rather impractical. Different methods have thus been suggested for collecting only a fraction of the total amount of used dialysis fluid. According to one suggested method the used dialysis fluid is passed through a container with twenty-five identical holes. The fluid is retained in one of the twenty-five holes, while the rest of the fluid is discarded in a drain. A problem with this method is that it is very difficult to provide and maintain twenty-five holes of exactly the same size, but doing so is necessary in order to obtain a correct determination of the total volume. Moreover, the collected volume is far too large to be practical. For example, during a treatment of five hours this amount can be up to six liters. It is also not possible to increase the number of holes in order to reduce this volume. This would pose additional difficulties in determining the total volume.

In the article "Urea Kinetic Modelling by Partial Dialysate Collection," in *The International Journal of Artificial Organs*, vol. 12, no. 2, 1980, pp. 96–102 by L. J. Garred, M. Rittau, W. McCready and B. Canaud, there is described a process for calculation of the amount of urea removed from the patient in which a sample is extracted downstream of the dialyzer. This sample can then be analyzed, after which the total amount of released urea can be calculated by multiplying the concentration in this sample by the total dialyzed amount from the dialyzer, which obviously must be determined by means of an estimation. Such an estimation, however, is difficult to perform, since the amount of dialysis fluid pumped into the dialyzer does not have to correspond with the entered value. Furthermore, in using this method one has to either measure or estimate the degree of ultrafiltration which takes place in the dialyzer. In this article, it is stated that one makes use of "timed collection" several times in order to arrive at an average value. This requires a constant total flow, i.e., also a constant ultrafiltration, something which is difficult to achieve, especially with hemofiltration and hemodiafiltration.

SUMMARY OF THE INVENTION

In accordance with the present invention, these and other objects have now been met by the invention of a method of measuring the effect of extraction of a measurable substance such as urea from an extractable fluid such as blood by means of an extraction fluid such as a dialysis fluid comprising extracting the measurable substance from the extractable fluid with the extraction fluid in a fluid extractor such as a dialyzer so as to produce a used extraction fluid including the measurable substance, measuring the total amount of the used extraction fluid, withdrawing a fraction of the used extraction fluid downstream of the fluid extractor, measuring the measurable substance in the fraction of the used extraction fluid, and calculating the total amount of the measurable substance removed by the extraction fluid by means of the measured value of the total amount of the used extraction fluid and the measured value of the measurable substance in the fraction of the used extraction fluid.

In accordance with one embodiment of the method of the present invention, the withdrawal of the fraction of the used extraction fluid is carried out by means of a pump.

In accordance with another embodiment of the method of the present invention, the amount of the used extraction fluid comprises a first flow and the withdrawn fraction of the used extraction fluid comprises a second flow, the second flow comprising a portion of the first flow. Preferably, the first and second flows are continuous, and in a preferred embodiment the second flow is from about one twentieth to about one twenty-thousandth of the first flow, preferably from about one two-hundredth to about one ten-thousandth of the first flow, and most preferably about one five-thousandth of the first flow.

In accordance with another embodiment of the method of the present invention, the measurable substance itself can be e.g. urea, creatinine, phosphates, and/or beta2-microglobulin.

In accordance with a preferred embodiment, the method includes initiating the withdrawing of a fraction of used dialysis fluid after determining that the blood has reached the dialyzer, whereby the measuring of the total amount of the used dialysis fluid and the withdrawing of the fraction of used dialysis fluid begins substantially simultaneously.

In accordance with another embodiment of the method of the present invention, the withdrawing of the fraction of the used extraction fluid with the pump is conducted intermittently. Preferably, the number of intermittent withdrawals of the fraction of the used extraction fluid is at least about ten, preferably at least about fifty, and most preferably at least about one hundred. In a preferred embodiment, the amount of used extraction fluid comprises a first flow and the withdrawn fraction of the used extraction fluid comprises a second flow, the second flow comprising a portion of the first flow. In one embodiment the withdrawing of the fraction by means of the pump is carried out at a constant speed for time periods which are proportional to the flow of the total amount of the used extraction fluid.

In accordance with another embodiment of the method of the present invention, the method includes measuring the total volume of the fraction of the used extraction fluid and measuring the total amount of measurable substance in said fraction so that the concentration of the measurable substance in the used extraction fluid can be calculated.

In accordance with another embodiment of the method of the present invention, the measurable substance is also contained in the extraction fluid, and the method includes calculating the amount of the measurable substance in the extraction fluid, based on known and/or entered dialysis parameters.

In accordance with this invention, a method is proposed for measuring the effect of a dialysis treatment in which a fraction of the used dialysis fluid is extracted downstream of the dialyzer for analysis of at least one substance such as urea whereby the fraction of the dialysis fluid is extracted through a branch conduit containing a pump. This method is characterized by the fact that the total amount of the used dialysis fluid is measured, in that the concentration of the substance in the extracted fraction is measured and also the total amount of the substance removed from the patient is calculated with the help of these values. In this manner, there is no need to make an estimate of the total amount of used dialysis fluid, but use can be made of a measured value which can be obtained with great exactitude, for example, by continually measuring the total flow from the dialyzer and integrating this flow over time.

Preferably, the pump in the branch conduit is operated at a speed which provides a flow which is proportional to the flow in the main conduit upstream of the branching point for the branch conduit and downstream of the dialyzer. In this manner, it is guaranteed that the concentration in the extractor fraction will be the same as that in the total dialysis fluid. When the pump operates continuously, particularly accurate measured values are obtained. As is clear from the following disclosure, however, it can also be operated intermittently.

Further in accordance with this invention, the sampling pump can conveniently be started automatically or manually after that it has been established that a flow of blood has reached the dialyzer. At the same time, one would then start measurement of the total amount of used dialysis fluid inclusive of the extracted ultrafiltrate therein. Upon determination of the total amount of a substance extracted from or supplied to the patient which substance, such as, for example sodium, potassium, calcium, magnesium, chloride, glucose and sodium bicarbonate, is already present in the fluid supplied to the dialyzer, the amount and/or proportion of that substance supplied to the dialyzer is also calculated with the help of known and/or entered dialysis parameters.

The same principle can be used for determining the total amount of other substances extracted or supplied to a patient under medical treatment.

BRIEF DESCRIPTION OF THE FIGURE

The following detailed description may be more fully understood with reference to the accompanying drawing, in which a schematic diagram or representation of the principles of the present invention can be seen.

DETAILED DESCRIPTION

Referring to the FIGURE, reference numeral 1 denotes a conduit which is intended to direct the flow of used dialysis fluid from a dialyzer (not shown) to a drain 2. A flow meter 3 is arranged in the conduit 1. By means of this flow meter 3, the total flow in conduit 1 can be measured. Conveniently, this flow meter can also be used for measuring the ultrafiltrate, by comparing the total flow with the flow to the dialyzer. A display showing the measured values thus obtained is denoted by reference to numeral 4. Reference numeral 5 denotes a start and stop arrangement, which can either be manual or automatic, e.g., for use in response to a blood detector which is arranged just upstream of the dialyzer. A sampling pump is denoted by reference numeral 6, the pump 6 being arranged to supply a fraction of the flow in the main conduit 1 from a branching point 7, through a pre-branching conduit 8, to a sample connection vessel 9. A dashed line is denoted by reference numeral 10. Sampling can be undertaken by intermittent withdrawals of fractions of the used extraction fluid at least 10 times during the course at a run. More preferably, intermittent withdrawals can occur at least about 50 times and more preferably at least about 100 times. The dashed line being intended to show that the flow meter 3 can be arranged to control the pump 6 in order to provide a determined proportional relationship between the flow in the main conduit 1 and the flow in the branch conduit 8. Box 11 denotes means for measuring the measurable substance in the used extraction fluid, and in particular, the fraction thereof.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For examples, the above-described details can be arranged and combined with other measurement and control arrangements in a conventional dialysis monitor.

It should be noted that the fraction can also be extracted prior to measurement of the total flow, but that this must then be corrected for with the extracted flow.

It should be further noted that certain monitors for hemofiltration mix the extracted filtrate with non-used replacement fluid so that a large amount of this mixture is obtained from the monitor. The present invention can be used to special advantage in this type of process.

The expression "the total amount of used dialysis fluid" as used herein relates both to normal dialysis fluid as well as to the filtrate mixture or the pure filtrate which leaves the dialyzer (hemofilter) during hemodiafiltration or hemofiltration, respectively.

The accuracy of the measurement of the concentration or the total amount of the measurable substance in the withdrawn fraction can be increased by multiple measurements of the concentration, e.g., 10 times etc.

I claim:

1. A method of measuring the effect of a hemodialysis, hemodiafiltration or hemofiltration treatment, comprising: extracting a measurable substance from blood with a flow of a dialysis fluid in a dialyzer so as to produce a continuous flow of dialysate fluid including said measurable substance, continuously measuring the actual flow rate of said dialysate fluid whereby the total amount of said dialysate fluid is determined therefrom, continuously withdrawing a fraction of said dialysate fluid at a rate which always bears the same proportional relationship to said measured flow rate of said dialysate fluid such that the concentration of said measurable substance in said fraction is substantially the same as the concentration of said measurable substance in said dialysate fluid, said fraction being withdrawn downstream of said dialyzer, measuring the concentration of said measurable substance in said fraction, and calculating the total amount of said measurable substance removed by said dialysate fluid based on said total amount of said dialysate fluid and said concentration of said measurable substance in said fraction.

2. The method of claim 1, further comprising the step of collecting said fraction in a sample vessel and measuring the concentration of said measurable, substance in said sample vessel.

3. The method of claims 1 or 2 wherein the withdrawing of said fraction of said dialysate fluid is carried out by means of a pump.

4. The method of claims 1 or 2 wherein actual flow of said dialysate fluid comprises a first flow and said withdrawing of said fraction of said dialysate fluid comprises a second flow, the flow rate of said second flow being proportional to the flow rate of said first flow.

5. The method of claims 1 or 2 wherein the volume of said fraction is from about one twentieth to about one twenty-thousandth the volume of said dialysate fluid.

6. The method of claim 5 wherein said volume of said fraction is from about one two-hundredth to about one ten-thousandth of said volume of said dialysate fluid.

7. The method of claim 6 wherein said volume of said fraction is about one five-thousandth of said volume of said dialysate fluid.

8. The method of claims 1 or 2 wherein said measurable substance is selected from the group consisting of urea, creatinine, phosphates, and beta2-microglobulin.

9. The method of claims 1 or 2 further comprising initiating said withdrawing of said fraction of said dialysate fluid after determining that said blood has reached said dialyzer, whereby said measuring of the actual flow rate of said dialysate fluid and said withdrawing of said fraction of said dialysate fluid begin substantially simultaneously.

10. The method of claims 1 or 2 wherein said measurable substance comprises a compound selected from the group consisting of sodium, potassium, calcium, magnesium, chloride, glucose, and sodium bicarbonate.

11. The method of claims 1 or 2, wherein said measuring of said concentration of said measurable substance in said fraction comprises a plurality of measurements of said concentration of said measurable substance in said fraction.

12. The method of claims 1 or 2, wherein said total amount of said dialysate fluid is determined by continuously measuring the total dialysate flow and integrating the flow over time.

13. A method of measuring the effect of a hemodialysis, hemodiafiltration or hemofiltration treatment, comprising: extracting a measurable substance from blood with a flow of a dialysis fluid in a dialyzer so as to produce a continuous flow of dialysate fluid including said measurable substance, continuously measuring the actual flow rate of said dialysate fluid whereby the total amount of said dialysate fluid is determined therefrom, intermittently withdrawing a fraction of said dialysate fluid at a rate which always bears the same proportional relationship to said measured flow rate of said dialysate fluid such that the concentration of said measurable substance in said fraction is substantially the same as the concentration of said measurable substance in said dialysate fluid, said fraction being withdrawn downstream of said dialyzer, measuring the concentration of said measurable substance in said fraction, and calculating the total amount of said measurable substance removed by said dialysate fluid based on said total amount of said dialysate fluid and said concentration of said measurable substance in said fraction.

14. The method of claim 13, further comprising the step of collecting said fraction in a sample vessel and measuring the concentration of said measurable substance in said sample vessel.

15. The method of claims 13 or 14 wherein the withdrawing of said fraction of said dialysate fluid is carried out by means of a pump.

16. The method of claims 13 or 14 wherein said actual flow of said dialysate fluid comprises a first flow and said withdrawing of said fraction of said dialysate fluid comprises a second flow, the flow rate of said second flow being proportional to the flow rate of said first flow.

17. The method of claims 13 or 14 wherein the volume of said fraction is from about one twentieth to about one twenty-thousandth the volume of said dialysate fluid.

18. The method of claim 17 wherein said volume of said fraction is from about one two-hundredth to about one ten-thousandth of said volume of said dialysate fluid.

19. The method of claim 18 wherein said volume of said fraction is about one five-thousandth of said volume of said dialysate fluid.

20. The method of claims 13 or 14 wherein said measurable substance is selected from the group consisting of urea, creatinine, phosphates and beta2-microglobulin.

21. The method of claims 13 or 14 further comprising initiating said withdrawing of said fraction of said dialysate fluid after determining that said blood has reached dialyzer, whereby said measuring of the actual flow rate of said dialysate fluid and said withdrawing of said fraction of said dialysate fluid begin substantially simultaneously.

22. The method of claims 13 or 14 wherein the number of said intermittent withdrawals of said fraction of said dialysate fluid is at least about ten.

23. The method of claim 22 wherein the number of said intermittent withdrawals of said fraction of said dialysate fluid is at least about fifty.

24. The method of claim 23 wherein the number of said intermittent withdrawals of said fraction of said dialysate fluid is at least about one hundred.

25. The method of claims 13 or 14 wherein said withdrawing of said fraction by means of said pump is carried out at a constant pump speed for time periods which are proportional to the measured flow rate of said dialysate fluid.

26. The method of claims 13 or 14 wherein said measurable substance comprises a compound selected from the group consisting of sodium, potassium, calcium, magnesium, chloride, glucose and sodium bicarbonate.

27. The method of claims 13 or 14 wherein said measuring of said concentration of said measurable substance in said fraction comprises a plurality of measurements of said concentration of said measurable substance in said fraction.

28. The method of claims 13 or 14, wherein said step of determining the total amount of said dialysate fluid is accomplished by continuously measuring the total dialysate flow rate and integrating the flow rate over time.

29. A method of measuring the effect of a hemodialysis, hemodiafiltration or hemofiltration treatment, comprising: extracting a measurable substance from blood with a flow of a dialysis fluid in a dialyzer so as to produce a continuous flow of dialysate fluid including said measurable substance, continuously measuring the actual flow rate of said dialysate fluid whereby the total amount of said dialysate fluid is determined therefrom, continuously withdrawing a fraction of said dialysate fluid at a rate which always bears the same proportional relationship to said measured flow rate of said dialysate fluid such that the concentration of said measurable substance in said fraction is substantially the same as the concentration of said measurable substance in said dialysate fluid, said fraction being withdrawn downstream of said dialyzer, measuring the total volume of said fraction of said dialysate fluid and the total amount of said measurable substance in said fraction of said dialysate fluid, whereby the concentration of said measurable substance in said dialysate fluid can be calculated and calculating the total amount of said measurable substance removed by said dialysate fluid based on said total amount of said dialysate fluid and said concentration of said measurable substance in said fraction.

30. The method of claim 29, further comprising the step of collecting said fraction in a sample vessel and measuring both the total amount of said measurable substance in said sample vessel and the total volume in said sample vessel.

31. The method of claims 29 or 30 wherein the withdrawing of said fraction of said dialysate fluid is carried out by means of a pump.

32. The method of claims 29 or 30 wherein said actual flow of said dialysate fluid comprises a first flow and said withdrawing of said fraction of said dialysate fluid comprises a second flow, the flow rate of said second flow being proportional to the flow rate of said first flow.

33. The method of claims 29 or 30 wherein the volume of said fraction is from about one twentieth to about one twenty-thousandth the volume of said dialysate fluid.

34. The method of claim 33 wherein said volume of said fraction is from about one two-hundredth to about one ten-thousandth of said volume of said dialysate fluid.

35. The method of claim 34 wherein said volume of said fraction is about one five-thousandth of said volume of said dialysate fluid.

36. The method of claims 29 or 30 wherein said measurable substance is selected from the group consisting of urea, creatinine, phosphates and beta2-microglobulin.

37. The method of claims 29 or 30 further comprising initiating said withdrawing of said fraction of said dialysate fluid after determining that said blood has reached dialyzer, whereby said measuring of the actual flow rate of said dialysate fluid and said withdrawing of said fraction of said dialysate fluid begin substantially simultaneously.

38. The method of claims 29 or 30 wherein said measurable substance comprises a compound selected from the group consisting of sodium, potassium, calcium, magnesium, chloride, glucose and sodium bicarbonate.

39. The method of claims 29 or 30 wherein said measuring of said concentration of said measurable substance in said fraction comprises a plurality of measurements of said concentration of said measurable substance in said fraction.

40. The method of claims 29 or 30, wherein said step of determining the total amount of said dialysate fluid is accomplished by continuously measuring the total dialysate flow rate and integrating the flow rate over time.

41. A method of measuring the effect of a hemodialysis, hemodiafiltration or hemofiltration treatment, comprising: extracting a measurable substance from blood with a flow of a dialysis fluid in a dialyzer so as to produce a continuous flow of dialysate fluid including said measurable substance, continuously measuring the actual flow rate of said dialysate fluid whereby the total amount of said dialysate fluid is determined therefrom, intermittently withdrawing a fraction of said dialysate fluid at a rate which always bears the same proportional relationship to said measured flow rate of said dialysate fluid such that the concentration of said measurable substance in said fraction is substantially the same as the concentration of said measurable substance in said dialysate fluid, said fraction being withdrawn downstream of said dialyzer, measuring the total volume of said fraction of said dialysate fluid and the total amount of said measurable substance in said fraction of said dialysate fluid, whereby the concentration of said measurable substance in said dialysate fluid can be calculated and calculating the total amount of said measurable substance removed by said dialysate fluid based on said total amount of said dialysate fluid and said concentration of said measurable substance in said fraction.

42. The method of claim 41, further comprising the step of collecting said fraction in a sample vessel and measuring both the total amount of said measurable substance in said sample vessel and the total volume in said sample vessel.

43. The method of claims 41 or 42 wherein the withdrawing of said fraction of said dialysate fluid is carried out by means of a pump.

44. The method of claims 41 or 42 wherein said actual flow of said dialysate fluid comprises a first flow and said withdrawing of said fraction of said dialysate fluid comprises a second flow, the flow rate of said second flow being proportional to the flow rate of said first flow.

45. The method of claims 41 or 42 wherein the volume of said fraction is from about one twentieth to about one twenty-thousandth the volume of said dialysate fluid.

46. The method of claim 45 wherein said volume of said fraction is from about one two-hundredth to about one ten-thousandth of said volume of said dialysate fluid.

47. The method of claim 46 wherein said volume of said fraction is about one five-thousandth of said volume of said dialysate fluid.

48. The method of claims 41 or 42 wherein said measurable substance is selected from the group consisting of urea, creatinine, phosphates and beta2-microglobulin.

49. The method of claims 41 or 42 further comprising initiating said withdrawing of said fraction of said dialysate fluid after determining that said blood has reached dialyzer, whereby said measuring of the actual flow rate of said dialysate fluid and said withdrawing of said fraction of said dialysate fluid begin substantially simultaneously.

50. The method of claims 41 or 42 wherein the number of said intermittent withdrawals of said fraction of said dialysate fluid is at least about ten.

51. The method of claim 50 wherein the number of said intermittent withdrawals of said fraction of said dialysate fluid is at least about fifty.

52. The method of claim 51 wherein the number of said intermittent withdrawals of said fraction of said dialysate fluid is at least about one hundred.

53. The method of claims 41 or 42 wherein said withdrawing of said fraction by means of said pump is carried out at a constant pump speed for time periods which are proportional to the measured flow rate of said dialysate fluid.

54. The method of claims 41 or 42 wherein said measurable substance comprises a compound selected from the group consisting of sodium, potassium, calcium, magnesium, chloride, glucose and sodium bicarbonate.

55. The method of claims 41 or 42 wherein said measuring of said concentration of said measurable substance in said fraction comprises a plurality of measurements of said concentration of said measurable substance in said fraction.

56. The method of claims 41 or 42 wherein said step of determining the total amount of said dialysate fluid is accomplished by continuously measuring the total dialysate flow rate and integrating the flow rate over time.

* * * * *

UNITED STATES PATENT AND TRADEMARK OFFICE
CERTIFICATE OF CORRECTION

PATENT NO. : 5,788,846
DATED : August 4, 1998
INVENTOR(S) : Sternby

It is certified that error appears in the above-identified patent and that said Letters Patent is hereby corrected as shown below:

Column 3, line 19, "microglobulin" should read --micro-globulin --.

Column 3, line 43, "substance in said" should read --substance of said--.

Column 3, line 50, "fluid, based" should read --fluid based--.

Column 5, line 46, "measurable, substance" should read --measurable substance--.

Column 5, line 67, "microglobulin" should read --micro-globulin --.

Column 6, line 46 "of said dialysate" should read --of dialysate--.

Column 7, line 55 "of said dialysate" should read --of dialysate--.

Column 8, line 52 "of said dialysate" should read --of dialysate--.

Signed and Sealed this

Twenty-third Day of February, 1999

Attest:

Q. TODD DICKINSON

*Attesting Officer*   *Acting Commissioner of Patents and Trademarks*